United States Patent [19]

Lin

[11] Patent Number: 5,702,391

[45] Date of Patent: *Dec. 30, 1997

[54] INTERVERTEBRAL FUSION DEVICE

[76] Inventor: Chih-I Lin, 14292 Spring Vista La., Chino Hills, Calif. 91709

[*] Notice: The term of this patent shall not extend beyond the expiration date of Pat. No. 5,578,035.

[21] Appl. No.: 442,095

[22] Filed: May 16, 1995

[51] Int. Cl.⁶ .................................................. A61B 17/70
[52] U.S. Cl. ................................ 606/61; 606/72; 606/60
[58] Field of Search ................................ 606/62, 64, 65, 606/66, 67, 68

[56] References Cited

FOREIGN PATENT DOCUMENTS 2733-826   1/1979   Germany .................................. 623/23

Primary Examiner—Michael Buiz
Assistant Examiner—Daphna Shai
Attorney, Agent, or Firm—Bacon & Thomas

[57] ABSTRACT

An intervertebral fusion device comprises a hollow tubular body, a plurality of stretching elements, an adjustment element, and an urging element. The tubular body is provided peripherally with a plurality of receiving holes in which the stretching elements are disposed movably. The adjustment element is disposed in the hollow interior of the tubular body such that inner ends of the stretching elements are urged by the adjustment element. The urging element is disposed in the hollow interior of the tubular body such that the adjustment element is urged at the top thereof by the bottom of the urging element, and that the adjustment element can be actuated by a rotational motion of the urging element so as to cause the stretching elements to jut out of the receiving holes for bringing about an increase in diameter of the tubular body.

4 Claims, 3 Drawing Sheets

FIG. 6a
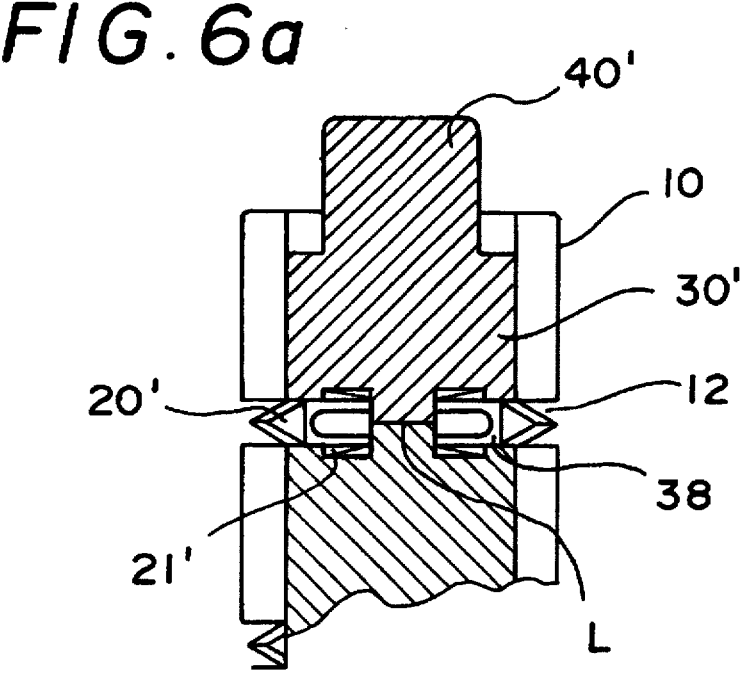
FIG. 6b
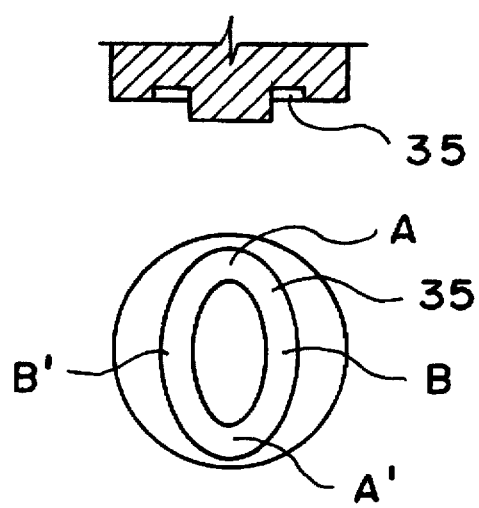
FIG. 6c
FIG. 6d
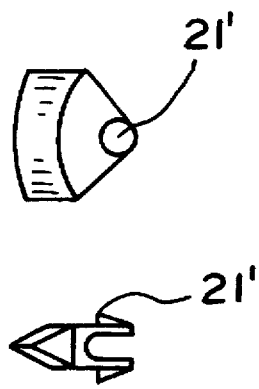
FIG. 6e

INTERVERTEBRAL FUSION DEVICE

FIELD OF THE INVENTION

The present invention relates generally to an orthopedic device, and more particularly to an intervertebral fusion system.

BACKGROUND OF THE INVENTION

The intervertebral fusion devices of the prior art are generally composed of a hollow cylindrical body provided peripherally with a plurality of holes in which bone grafts are held. The case in point is the BAK interbody fusion system, which is a product of Spintech Corporation of the United States and is an improvement over the similar systems disclosed respectively in the U.S. Pat. Nos. 4,501, 269 and 5,015,247. The BAK interbody fusion system comprises a rigid cylindrical body of a hollow construction and having an inflexible outer diameter which can not be adjusted as desired. As a result, two vertebrae which are intended to be fixed cannot be kept apart at an appropriate interval. The intervertebral fusion system disclosed in the U.S. Pat. No. 4,263,953 is composed of a cylindrical body which is not completely rigid and can not be yet adjusted diametrically so as to keep two vertebrae apart at an interval as required by the surgical operation. Such prior art intervertebral fusion systems as described above share a common defect in design in that the size of an incision made by a surgeon must be slightly larger than the outer diameter of the fusion system to be implanted, thereby prolonging the healing of the incised tissue.

SUMMARY OF THE INVENTION

It is therefore the primary objective of the present invention to provide an intervertebral fusion device having an adjustable outer diameter.

It is another objective of the present invention to provide an intervertebral fusion device comprising a hollow tubular body provided with a plurality of holes, a plurality of stretching elements, an adjustment element, and an urging element.

The hollow tubular body is provided at the top thereof with an opening and is further provided peripherally with a plurality of through holes communicating the hollow interior of the tubular body with the outside of the tubular body.

The stretching elements are adjustably received in the hollow tubular body via the through holes and are provided respectively with a holding means.

The adjustment element is located in the hollow interior of the tubular body such that the inner ends of the stretching elements are urged by the adjustment element.

The urging element is received axially in the hollow interior of the tubular body via the top opening of the tubular body such that the top end of the adjustment element is urged by the urging element, thereby enabling the urging element to actuate the adjustment element when the urging element is rotated, so as to cause the inner end of each stretching element to be urged by the adjustment element. As a result, the inner ends of the stretching elements are separated from the axis of the tubular body by various distances so as to accomplish the diameter adjustment of the intervertebral fusion device of the present invention.

The tubular body or the adjustment element is provided with a retaining means engageable with the holding means of the stretching elements for preventing the stretching elements from becoming disengaged from the tubular body via the through holes of the tubular body.

The tubular body of the present invention has a circular cross section and a hollow interior capable of accommodating the adjustment element. The hollow interior is preferably regular polygonal or circular in cross section. The tubular body of the present invention is preferably a cylindrical body having a regular polygonal profile.

The tubular body is provided with 3–8, preferably 3–6, peripheral surfaces, each of which is in turn provided with 2–8, preferably 2–6, through holes. The peripheral surfaces are spaced equidistantly. The through holes of the same peripheral surface are preferably located at the same cross-sectional surface. It is suggested that the peripheral surfaces are provided with the through holes, which are corresponding in number to one another. The through holes may be arranged alternately or correspondingly.

The stretching elements may be columnar or cylindrical in shape and have an arcuate outer end having a considerable curvature. The stretching elements are provided respectively with a holding means engageable with the retaining means of the adjustment element or the tubular body. The holding means of the stretching elements is preferably located in the vicinity of the outer end of the stretching elements if the retaining means is provided on the tubular body. The holding means of the stretching elements is preferably located in the proximity of the inner ends of the stretching elements if the retaining means is provided on the adjustment element.

The adjustment element of the present invention is similar in construction to a corrugated shaft or eccentric bearing and is variable in diameter when the adjustment element is moved forward or backward. The corrugated shaft is provided with a plurality of spherical bodies or oblong bodies, which are in contact with one another with or without joining together to form an united body. The eccentric bearing comprises an eccentric circular track or oblong track.

When the corrugated shaft is used as the adjustment element, the retaining means is preferably located at the outer ends of the through holes of the tubular body. The retaining means may be a hole which is so made as to have a smaller outer diameter. It is also suggested that the tubular body may be provided with a casing having a plurality of arresting holes. The holding means of the stretching element may be an object which is greater in diameter than the arresting holes.

When the eccentric bearing is used as the adjustment element, the outer holes of the eccentric segment of the eccentric bearing may be used as arresting holes. The holding means of the stretching element may be an object which is greater in diameter than the arresting holes.

The object, which was referred to above, may be a resilient object capable of jutting out of the stretching elements by itself after being pressed into the stretching elements and released.

The urging element is disposed in the tubular body via the top opening of the tubular body such that the urging element can be turned to adjust the position of the adjustment element so as to regulate the extent to which the stretching elements are jutted out of the tubular body via the through holes. For example, if a screw is used as an urging element, the top opening of the tubular body should be provided on the inner wall thereof with threads engageable with the screw. On the other hand, the adjustment element is composed of a plurality of spherical bodies whose positions can be regulated by the extent to which the screw is advanced. In other words, when the screw is advanced into the tubular body, the positions of the spherical bodies of the adjustment element are so adjusted as to cause the stretching elements to jut out via the through holes of the tubular body. If an eccentric bearing is used as the adjustment element, the urging element may be columnar in construction and is made integrally with the adjustment element.

It is therefore readily apparent that the position of the adjustment element is regulated by the urging element, and that the stretching elements of the present invention are indirectly caused to jut out of the tubular body via the through holes when the adjustment element is adjusted by the urging element in motion. As a result, the outer diameter of the intervertebral fusion device of the present invention can be so adjusted as to keep two vertebrae apart by an appropriate distance. In addition, the present invention permits a surgeon to make a relatively small incision for implanting the device. For example, the intervertebral fusion device of the present invention having a diameter of 12 mm can be used in place of the prior art intervertebral fusion device having a diameter of 16 mm, thanks to the stretching elements of the present invention which can be actuated to jut out of the tubular body in such a manner that the outer diameter of the intervertebral fusion device of the present invention is increased to 16 mm from 12 mm.

The foregoing objectives, features, functions and advantages of the present invention will be more readily understood upon a thoughtful deliberation of the following detailed description of the embodiments of the present invention in conjunction with the accompanying drawings.

BRIEF DESCRIPTION OF THE DRAWINGS

FIGS. 6a–6e are schematic views of a third preferred embodiment of the present invention.

DETAILED DESCRIPTION OF THE EMBODIMENTS

Figure 1:
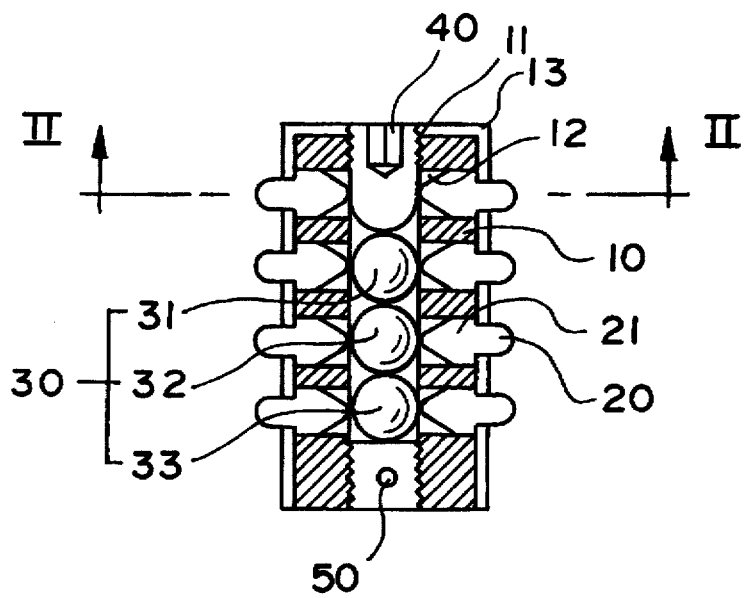
FIG. 1 shows a sectional view of a first preferred embodiment of the present invention.
Figure 2:
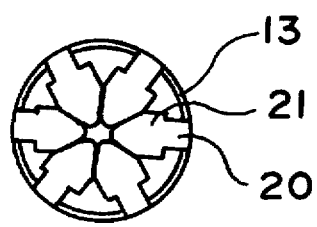
FIG. 2 shows a cross-sectional view taken along the line II—II as shown in FIG. 1.
Figure 3:
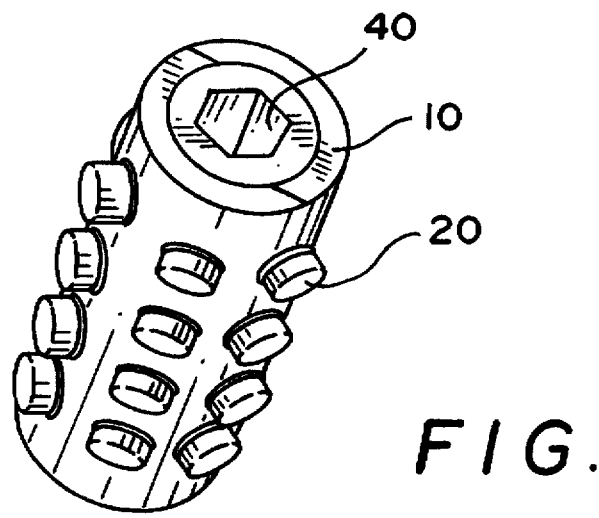
FIG. 3 shows a perspective view of the first preferred embodiment of the present invention.

As shown in FIGS. 1 to 3, an intervertebral fusion device of the first preferred embodiment of the present invention comprises a tubular body 10 of a hollow construction, a plurality of stretching elements 20, an adjustment element 30, and an urging element 40. The hollow tubular body 10 is provided at the top thereof with a threaded hole 11 and is further provided peripherally with a plurality of through holes 12 and a casing 13. The stretching elements 20 are provided respectively with a holding means 21. The adjustment element 30 is composed of three spherical bodies 31, 32 and 33. The tubular body 10 is further provided at the bottom thereof with a screw 50. All the stretching elements 20 are enclosed by the casing 13 when the urging element 40 (a screw) is not tightened as shown in FIG. 2.

Figure 4:
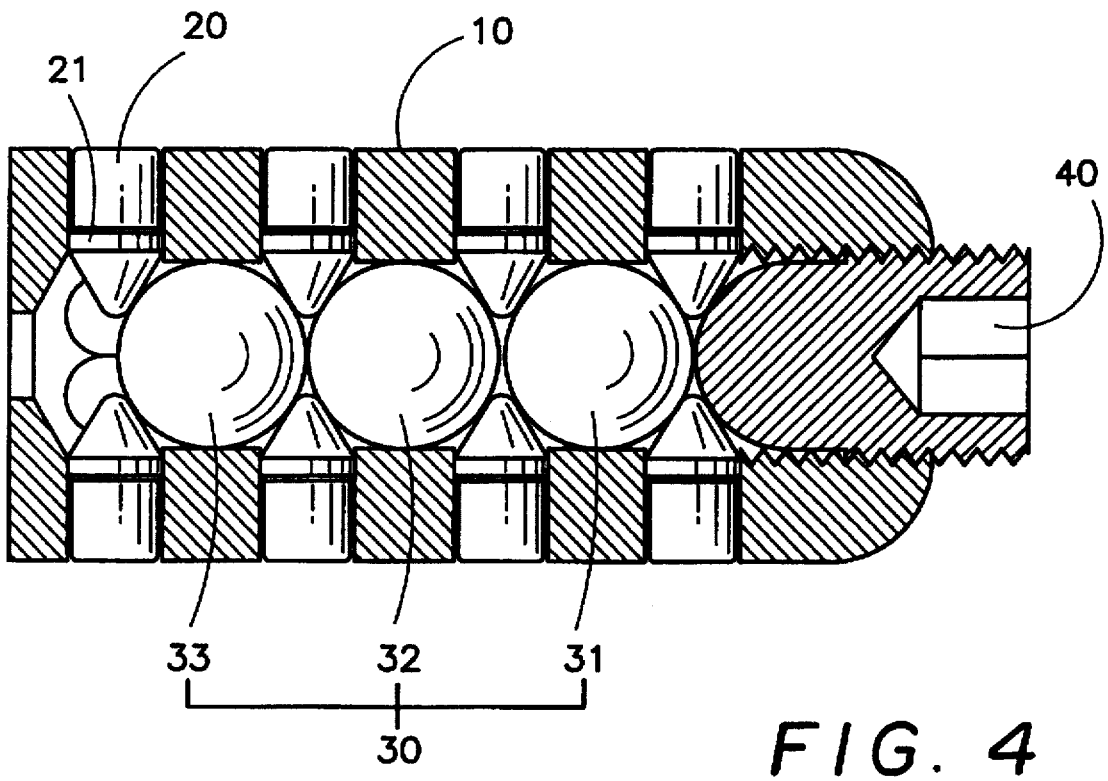
FIG. 4 is a schematic view showing that the stretching elements of a second preferred embodiment of the present invention are not caused to jut out.
Figure 5:
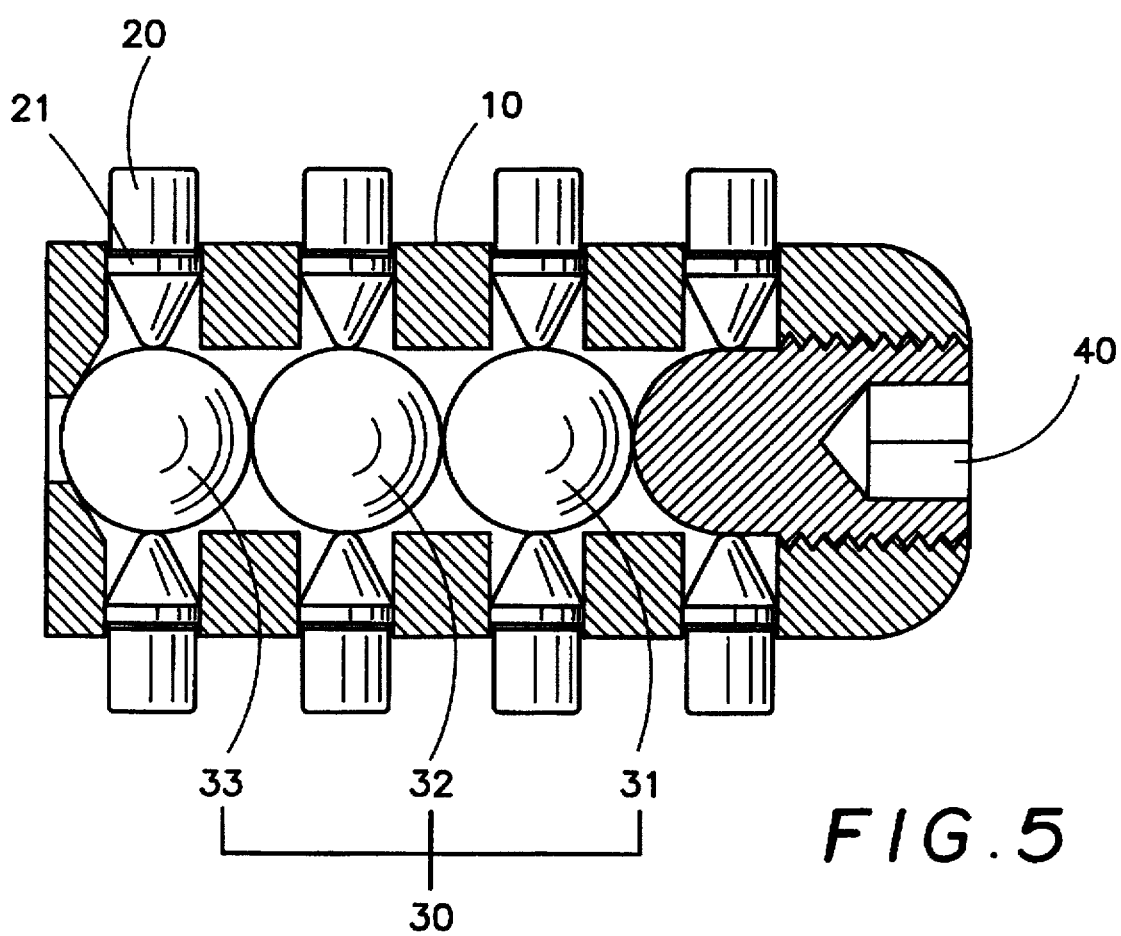
FIG. 5 is a schematic view showing that the stretching elements of the second preferred embodiment of the present invention are jutted out.

As shown in FIGS. 4 and 5, the second preferred embodiment of the present invention is different from the first preferred embodiment of the present invention in that the former is devoid of the bottom screw 50. The reference numerals of 10, 20, 21, 30, 31, 32, 33 and 40 are similar in definition to the like reference numerals of FIG. 1.

As illustrated in FIG. 4, the urging element 40 is not tightened so that all stretching elements 20 are forced by the vertebra into the tubular body 10. When the urging element 40 is tightened, the spherical bodies 31, 32 and 33 to exert a pressure on the bottom of the tubular body 10 as well as the tapered portions of the stretching elements 20. As a result, the stretching elements 20 are caused to jut out, as shown in FIG. 5. The outer diameter of the intervertebral fusion device of the present invention is therefore so increased as to cause the device to press intensively against the vertebrae.

The third preferred embodiment of the present invention is illustrated in FIGS. 6a–6e, in which the reference numerals 20', 21', 30' and 40' are similar in definition to the like reference numerals without an apostrophe of FIG. 1. The third preferred embodiment of the present invention is provided with an eccentric bearing 30' serving as the adjustment element and having a retaining means 38. As shown in FIG. 6a, the eccentric bearing 30' and the urging element 40' are made integrally. As illustrated in FIGS. 6a–6e, when the eccentric bearing 30' is actuated by the rotational motion of the urging element 40' such that the oblong slot 35 of the eccentric bearing 30' is caused to retain the holding element 21' of the stretching element 20' at the point B or B', the stretching element 20' in question is contained in its entirety in the through hole 12 of the tubular body 10. As the intervertebral fusion device of the present invention is implanted, the urging element 40' is so rotated as to actuate the eccentric bearing 30' in such a manner that the holding elements 21' of the stretching elements 20' are retained at the points A and A' by the oblong slot 35 of the eccentric bearing 30', and that the stretching elements 20' are caused to jut out of the through holes 12 of the tubular body 10 to urge intensively the vertebrae.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. An intervertebral fusion device comprising:
   a cylindrical body of a hollow construction and having at a top thereof an opening and further having axially a hollow interior, said cylindrical body provided peripherally with a plurality of through holes communicating the outside of said cylindrical body with said hollow interior of said cylindrical body;
   a plurality of stretching elements disposed respectively and movably in said through holes of said cylindrical body such that said stretching elements can be caused to jut out of said through holes, said stretching elements provided respectively with a holding means capable of preventing said stretching elements from becoming disengaged from the cylindrical body;
   an adjustment element disposed in said hollow interior of said cylindrical body such that inner ends of said stretching elements are urged by said adjustment element wherein said adjustment element comprises a plurality of separate and discrete members in contact with each other; and
   an urging element inserted into said hollow interior of said cylindrical body via said opening located at the top of said cylindrical body such that said adjustment element can be actuated by a rotational motion of said urging element so as to force said stretching elements to extend out of said through holes of said cylindrical body to bring about an increase in diameter of said cylindrical body;

wherein one of said hollow cylindrical body and said adjustment element is provided with a retaining means engageable securely with said holding means of said stretching elements for preventing said stretching elements from becoming disengaged from said cylindrical body via said through holes.

2. The intervertebral fusion device as defined in claim 1, wherein said adjustment element comprises a plurality of spherical bodies making contact with one another.

3. The intervertebral fusion device as defined in claim 1, wherein said opening located at the top of said cylindrical body is a threaded hole; and wherein said urging element is a fastening screw engaged with said threaded hole.

4. The intervertebral fusion device as defined in claim 1, wherein said adjustment element comprises a plurality of oblong bodies making contact with each other.

* * * * *